United States Patent
Tsai et al.

[11] Patent Number: 5,366,656
[45] Date of Patent: Nov. 22, 1994

[54] OPTICALLY ACTIVE ALCOHOL AND DERIVATIVES THEREOF, LIQUID CRYSTAL COMPOSITION CONTAINING SAME AND LIQUID CRYSTAL DEVICE

[75] Inventors: Wen-Liang Tsai, Hsinchu; Shu-Hui Yang, Taipei, both of Taiwan, Prov. of China

[73] Assignee: Industrial Technology Research Institute, Taiwan, Prov. of China

[21] Appl. No.: 201,393

[22] Filed: Feb. 24, 1994

Related U.S. Application Data

[63] Continuation-in-part of Ser. No. 830,134, Jan. 31, 1992, abandoned.

[51] Int. Cl.$^5$ .............. C09K 19/52; C09K 19/12; C07C 69/76; C07C 43/02
[52] U.S. Cl. .............. 252/299.01; 252/299.64; 252/299.65; 252/299.66; 252/299.67; 560/59; 560/61; 560/64; 560/65; 568/631; 568/642; 568/644; 568/645
[58] Field of Search .............. 252/299.01, 299.64, 252/299.65, 299.66, 299.67; 560/59, 61, 62, 64, 65; 568/631, 642, 644, 645

[56] References Cited

U.S. PATENT DOCUMENTS 4,812,259  3/1989  Yoshinaga et al. ............ 252/299.65
4,961,875  10/1990  Ohno et al. ............ 252/299.66

FOREIGN PATENT DOCUMENTS 63-254182  10/1988  Japan.

OTHER PUBLICATIONS

Booth, C. J. et al. "New Chiral Liquid Crystals Derived from (R)-2-(4-Hydroxyphenoxy) propan-1-ol", The 14th International Liquid Crystal Conference, Jun. 21-26, 1992.

Booth, C. J. et al. "Fluoro-Substituted Chiral Liquid Crystals Derived From (R)-2-(4-Hydroxyphenoxyl) propan-1-ol", The 14th International Liquid Crystal Conference, Jun. 21-26, 1992.

Rappaport, A. G. et al. "X-Ray Scattering Studies of a Large Electroclinic Effect Material", The 14th International Liquid Crystal Conference, Jun. 21-26, 1992.

Walba, D. M. et al. "Electronic Nonlinear Optics in Ferroelectric Liquid Crystals", The 14th International Liquid Crystal Conference, Jun. 21-26, 1992.

Lackner, A. M., et al. "Properties of new ferroelectric materials", Liquid Crystals, 5(4):1259-1267 (1989).

Otterhold, B. et al. "Synthesis and Electro-Optical Properties of Some Ferroelectric Liquid Crystals Derived from Lactic Acid" *mol. Cryst. Liq. Cryst.* 146:189-216 (1987).

*Primary Examiner*—Wu: Shean
*Attorney, Agent, or Firm*—Ladas & Parry

[57] ABSTRACT

Optically active compounds of general formulae

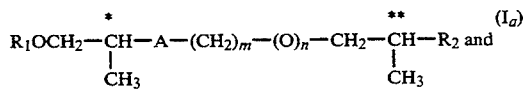

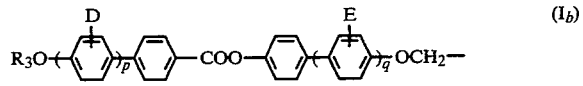

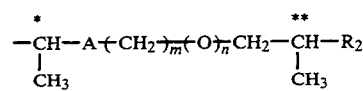

wherein A is O or S, $R_1$ is a hydrogen atom, an alkyl group having 1-22 carbon atoms, a hydroxy containing alkyl group, para-alkyl substituted phenyl, para-alkyl substituted biphenyl, hydroxyphenyl, hydroxybiphenyl or tosyl; $R_2$ is an alkyl group having 2-8 carbon atoms; m is an integer of 0-5, n is 0 or 1, where when m=0, n is not 1; p is 0 or 1; q is 0 or 1; D and E are independently H or a halogen atom; $R_3$ is a linear alkyl group having 1 to 22 carbon atoms; and * and ** are asymmetric centers.

28 Claims, No Drawings

OPTICALLY ACTIVE ALCOHOL AND DERIVATIVES THEREOF, LIQUID CRYSTAL COMPOSITION CONTAINING SAME AND LIQUID CRYSTAL DEVICE

This application is a continuation-in-part application of U.S. patent application Ser. No. 07/830,134 which was filed on Jan. 31, 1992 and which is abandoned.

BACKGROUND OF THE INVENTION

Field of the Invention

This invention relates to optically active alcohols and their derivatives having two asymmetric centers, liquid crystal compositions containing said optically active compounds and liquid crystal devices thereof.

The technology of liquid crystal displays has been developed rapidly in the last two decades due to the invention of novel nematic liquid crystals, the discovery of their electro-optic effects and extensive development in electronic industries. The application of liquid crystal displays has been extended from the simple display in electronic watches to the display of personal computers and even has a great potential in the development of the display of high definition television. Although liquid crystals are of wide application, further improvements are desired so as to improve their contrast, view angle and their switching speed.

In 1975 Meyer et. al. found that chiral smecticC phase is ferroelectric after a series of experiments conducted on p-(decyloxy) benzylidene-amino-2-methylbutyl-cinnamate (R. B. Meyer, L. Liebert, L. Strzeleckl and P. Keller, "Ferroelectric Liquid Crystals" J. Physique Lett., 1975, 36, L69). Since then, the development and the application of such smectic phase liquid crystals have become a challenging research field. In 1980 Clark and Lagerwall invented a device employing such liquid crystals, i.e., an SSFLC (surface-stabilized ferroelectric liquid crystal) light valve which is a basic device for new electro-optic technology (N. A. Clark, S. T. Lagerwall, Appl. Phys. Lett., 1980, 36, 899). Since the ferroelectric liquid crystals exhibits unique switching speed and memorizable characteristics, they are in great demand for application in optical-switches, optical-calculators, flat displays, etc.

The ferroelectricity of ferroelectric liquid crystals are mainly contributed by the optically active molecular part of the liquid crystals formed by asymmetric synthesis. Ferroelectric liquid crystal displays generally employ a mixture of liquid crystals in which chiral compounds are used as chiral dopant. The chiral dopant may or may not have chiral smectic C phase (W. Kuczynski, H. Stegemeyer, Chem. Phys. Lett., 1980, 70, 123; F. Leenhouts, S. M. Kelly, A. villiger, Displays, 1990, 41). Intrinsically ferroelectric liquid crystal is also one of nonlinear optical which are now under intensive study worldwide.

Lactic acid is a commercially available optically active material which consists of easily convertible functional groups, i.e., hydroxy and carboxy groups, which can be easily converted into other molecular structures. U.S. Pat. Nos. 4,556,727, 4,812,259, 4,880,560, 4,961,875, and 4,985,172 disclose optically active lactic derivatives and their application in liquid crystal compositions and liquid crystal devices. These patents also disclose that liquid crystal materials containing two asymmetric centers have better physical properties than those containing only one asymmetric center.

SUMMARY OF THE INVENTION

An object of this invention is to provide optically active alcohols having two asymmetric centers and their derivatives which are novel ferroelectric liquid crystals and which exhibit excellent physical characteristics when used in liquid crystal compositions and liquid crystal devices.

In one aspect of the invention, the optically active compounds containing two asymmetric centers according to the present invention have the following general formula:

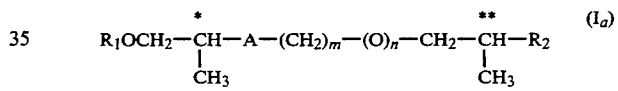

$$R_1OCH_2-\overset{*}{\underset{CH_3}{CH}}-A-(CH_2)_m-(O)_n-CH_2-\overset{**}{\underset{CH_3}{CH}}-R_2 \quad (I_a)$$

wherein A is O or S, $R_1$ is a hydrogen atom, an alkyl group having 1-22 carbon atoms, a hydroxy containing alkyl group, para-alkyl substituted phenyl, para-alkyl substituted biphenyl, hydroxyphenyl, hydroxybiphenyl or tosyl; $R_2$ is an alkyl group having 2-8 carbon atoms; m is an integer of 0-5; n is 0 or 1, where when m=0, n is not 1, and , and ** are asymmetric centers.

Preferabe optically active organic compounds of formula (Ia) are as follows:

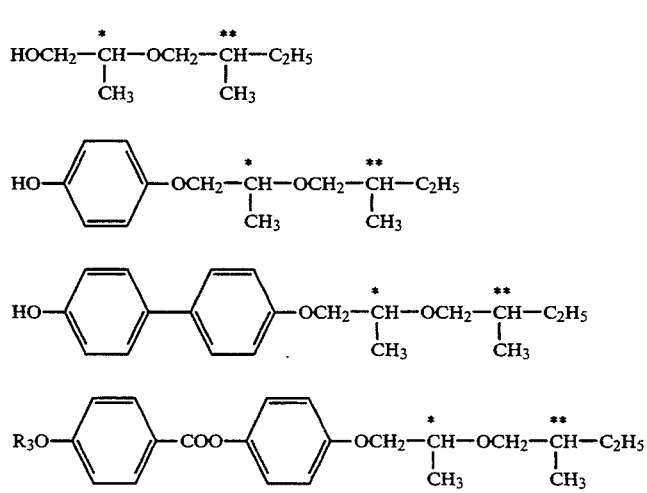

-continued

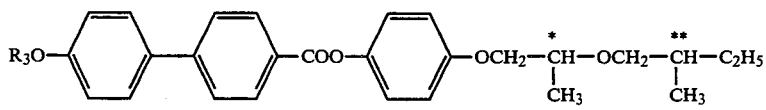

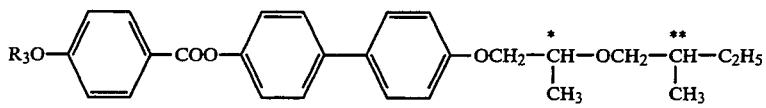

In another aspect of the invention, an optically active organic compound having the formula:

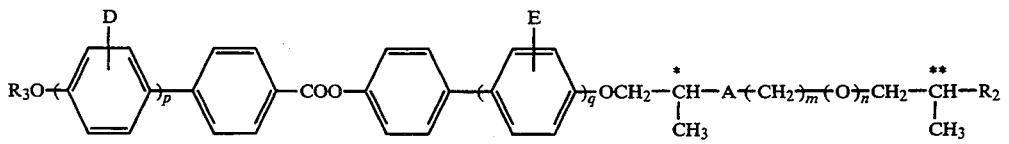

wherein A is O or S; $R_2$ is an alkyl group having 2–8 carbon atoms; m is an integer of 0–5; n is 0 or 1, where when m=0, n is not 1; p is 0 or 1; q is 0 or 1; D and E are independently H or a halogen atom; $R_3$ is a linear alkyl group having 1 to 22 carbon atoms; and * and ** are asymmetric centers. Preferably, $R_3$ is a linear alkyl having 3–12 carbon atoms.

The compounds of formula $(I_a)$ are optically active alcohols which are prepared from lactic acid and thiolactic acid. In preparation, a lactic acid or a thiolactic acid is first esterified and the resulting ester is etherified by reacting the hydroxy group or the hydrogen sulfide group thereof with a chiral alkyl halide or alkyl sulfonate. A subsequent reduction reaction provides an optically active alcohol. The combination of monobenzyl ether of hydroquinone or 4,4'-biphenol with the resulting optically active alcohol can be realized by a substitution reaction in which a sulfonate of the optically active alcohol is reacted with the monobenzyl ether of hydroquinone or 4,4'-biphenol respectively. After hydrogenation, the chiral compounds containing hydroquinone and 4,4-biphenol are obtained.

The organic compounds obtained according to the present invention which contain hydroquinone and 4,4'-biphenol can be used to prepare ferroelectric liquid crystals. The preparation thereof comprises the esterification of the organic alcohol with other organic acids or acid chlorides which may or may not have liquid crystal phase.

The liquid crystal composition according to the present invention may be a mixture of compounds of formula $(I_a)$ and/or compounds of formula $(I_b)$, as well as a mixture of the compounds of formula $(I_a)$ and/or of formula $(I_b)$ and other liquid crystals containing smectic C phase or chiral smectic C phase. The liquid crystal device according to the present invention comprises two substrate plates which sandwich the liquid composition prepared from the compounds of formula $(I_a)$ and/or $(I_b)$. The liquid crystal material according to the present invention can be used to fabricate a light valve, an optically computing element or a non-linear optical material. The liquid crystals prepared from the optically active organic compounds containing two asymmetric centers according to the present invention exhibit improved liquid crystal characteristics.

Hereinbelow, the present invention will be explained more specifically by way of examples.

EXAMPLE 1

Preparation of para-decyloxy benzoic acid 2.11 g of sodium hydroxide was dissolved in 50 ml of ethyl alcohol and to the solution were added 2.6 g of para-hydroxy benzoic acid and 5.8 ml of 1-bromodecane. After the mixture was refluxed for 15 hours, 25 ml of 10% aqueous sodium hydroxide solution was added and refluxed for another two hours. After cooling, concentrated HCl was dropped into the solution until it was acidic. Filtration and recrystallization from ethyl alcohol gave 3.8 g of pure product (yield 73%).

EXAMPLE 2

Preparation of para-dodecyloxy benzoic acid 4.17 g of sodium hydroxide was dissolved in 100 ml of ethyl alcohol. Then, 5.03 g of para-hydroxy benzoic acid and 12.2 ml of 1-bromododecane were added to the solution and refluxed for 15 hours. 50 ml of 10% aqueous sodium hydroxide solution was added and refluxed for another 2 hours. After cooling, concentrated HCl was dropped into the solution until it was acidic. Filtration and recrystallization from ethyl alcohol gave 7.66 g of pure product (yield 70%).

EXAMPLE 3

Preparation of 4-(4-octyloxyphenyl) benzoic acid 1.15 g of sodium hydroxide was dissolved in 100 ml of ethyl alcohol. Then, 2.0 g of 4-(4'-hydroxyphenyl) benzoic acid and 2.45 ml of 1-bromooctane were added to the solution and refluxed for 16 hours. 50 ml of 10% aqueous sodium hydroxide solution was added and refluxed for another 2 hours. After cooling, concentrated HCl was dropped into the solution until it was acidic. Filtration and recrystallization from ethyl alcohol gave 1.95 g of pure product (yield 64%).

EXAMPLE 4

Preparation of 4-(4'-nonyloxyphenyl) benzoic acid 1.12 g of sodium hydroxide was dissolved in 100 ml of ethyl alcohol. Then, 2.0 g of 4-(4'-hydroxyphenyl) benzoic acid and 2.3 ml of 1-bromononane were added to the solution and refluxed for 19 hours. 50 ml of 10% aqueous sodium hydroxide solution was added and refluxed for another two hours. After cooling, concentrated HCl was dropped into the solution until it was acidic. After filtration and recrystallization from ethyl alcohol gave 2.18 g of pure product (yield 69%).

EXAMPLE 5

Preparation of 2(S)-[2(S)-methylbutloxy]propionic acid ethyl ester

A mixture of 7.2 g of lactic acid ethyl ester, 14.14 g of 1-iodo-2-methylbutane and 17.0 g of silver oxide were heated at 70 deg C and stirred for 12 hours. After the filtration of the resulting product, the filtrate was purified by vacuum distillation, affording 5.9 g of pure product (yield 52%).

$[\alpha]_D^{22} = -56.3°$, (C=1.05, $C_2H_5OH$)

EXAMPLE 6

Preparation of a compound of formula (Ia), wherein A=O, m and n are 0, $R_1$=H, $R_2$=$C_2H_5$ 4.8 g of 2(S)-[2(S)-methylbutyloxy]propionic acid ethyl ester was dissolved in ethyl ether. Then, an ether solution of lithium aluminum hydride was added dropwise to the solution under stirring. After 7 hours of stirring, a small amount of water was further added and the product was extracted with dicholomethane. The organic layer purified by flash chromatography gave 2.8 g (yield 77%) of the final product.

$[\alpha]_D^{22} = 20.2°$ (C=1.01, EtOH)

EXAMPLE 7

Preparation of a compound of formula (Ia), wherein A=O, m and n are 0,

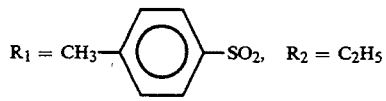

0.35 g of 2(S)-[2(S)-methylbutyloxy] propanol was dissolved in pyridine. The solution was reacted with 0.73 g of tosyl chloride at 0 deg C. After the reaction was completed, a small amount of water was added and stirred for 1 hour. The mixture was extracted with ethyl ether. The ether phase was washed with a 10% HCl solution, saturated $NaHCO_3$ solution and water. After the ether phase was dried over sodium sulfate and concentrated, it gave 0.68 g of pure product (yield 95% ).

$[\alpha]_D^{20} = -1.5°$ (C=1.04, EtOH)
$[\alpha]_D^{20} = -1.5°$ (C=1.04, ETOH

EXAMPLE 8

Preparation of a compound of formula (Ia), wherein A=O, m and n are 0,

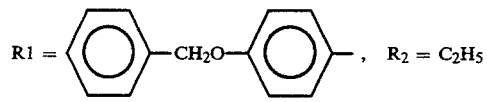

0.46 g of p-(benzyloxy)phenol was dissolved in a solution of sodium hydroxide (0.2 g) in ethanol. 0.68 g of the sulfonate prepared in Example 7 was added to the solution and refluxed for 24 hours. After extraction with dicholomethane and water, the extract was concentrated and purified by column chromatography to give 0.18 g of pure product (yield 70%).

$[\alpha]_D^{22} = -2.0°$ (c=1.00, EtOH)

EXAMPLE 9

Preparation of a compound of formula (Ia), wherein A=O, m and n are 0,

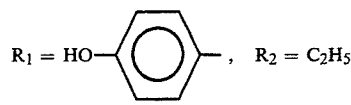

1.21 g of the product prepared in Example 8 was dissolved in ethyl alcohol. After hydrogenation of the solution and purification by column chromatography, 0.72 g (yield 76%) of the product was obtained.

$[\alpha]_D^{25} = -2.2°$ (C=0.98, EtOH)

EXAMPLE 10

Preparation of a compound of formula ($I_b$), wherein A=O, D=H, m,n, p and q are O, $R_2$=$C_2H_5$, $R_3$=$C_{10}H_{21}$ 98.5 mg of the product prepared in Example 9,460 mg of p-decyloxy benzoic acid, 6.1 mg of p-dimethylamino pyridine, and 85.8 mg of 1,3-dicyclohexyl-carbodiimide were mixed with 4 ml of dichloromethane at room temperature. After the reaction was completed, the reaction solution are filtered and concentrated. Purification by flash column chromatography gave 118 mg of pure product (yield 62%) .

$[\alpha]_D^{20} = -2.5°$ (C=0.48, EtOH)

EXAMPLE 11

Preparation of a compound of formula ($I_b$), wherein A=O, D=H, m, n, p and q are 0, $R_2$=$C_2H_5$, $R_3$=$C_{12}H_{25}$ Following the procedure of Example 10, 0.32 g (70% yield) of the product was obtained from 0.26 g of p-dodecyloxy benzoic acid, and 0.21 g of the product prepared in Example 9.

$[\alpha]_D^{20} = -2.2°$ (C=1.01, EtOH

EXAMPLE 12

Preparation of a compound of formula ($I_b$), wherein A=O, D=H, m=0, n=0, p=1, q=0, $R_2$ =$C_2H_5$ , $R_3$ =$C_8H_{17}$ Following the procedure of Example 10, 0.11 g (60% yield) of the product was obtained from 0.1 g of 4-(4'-octyloxyphenyl)benzoic acid and 82 mg of the product prepared in Example 9.

$[\alpha]_D^{20} = -4.5°$ (C=0.11, $CHCl_3$

EXAMPLE 13

Preparation of a compound of formula ($I_b$), wherein A=O, D=H, m=O, n=O, p=1, q=O, $R_2$=$C_2H_5$, $R_3$=$C_9H_{19}$ Following the procedure of Example 10, 0.31 g (72% yield) of the product was obtained from 0.27 g of 4-(4'-nonyloxyphenyl)benzoic acid and 0.20 g of the product prepared in Ex. 9.

$[\alpha]_D^{20} = -8.3°$ (C=1.00, $CHCl_3$)

EXAMPLE 14

Preparation of a compound of formula (Ib), wherein A=O, D=H, m=O, n=O, p=1, q=0, $R_2$=$C_2H_5$, $R_3$=$C_{10}H_{21}$ Following the procedure of Example 10, 0.2 g (53% yield) of the product was obtained from 0.23 g of 4-(4'-decyloxyphenyl)benzoic acid and 0.17 g of the product prepared in Example 9.

$[\alpha]_D^{23} = -5.4°$ (C=1.09, $CHCl_3$)

EXAMPLE 15

Preparation of a compound of formula (Ib), wherein A=O, D=H, m=0, n=0, p=1, q=0, $R_2=C_2H_5$, $R_3=C_{12}H_5$ Following the procedure of Example 10, 0.25 g (69% yield) of the product was obtained from 0.23 g of 4-(4'-dodecyloxyphenyl)benzoic acid and 0.16 g of the product prepared in Example 9.

$[\alpha]_D^{23} = -11.6°$ (C=1.00, CHCl$_3$)

TABLE 1

| $R_3$ | p | * | ** | C | $S_B$ | $S_C*$ | $S_A$ | I | |
|---|---|---|---|---|---|---|---|---|---|
| $C_{10}H_{21}$ | 0 | S | S | .28 | — | (.17) | (.22) | . | (Ex. 10) |
| $C_{12}H_{25}$ | 0 | S | S | .34 | — | (.19) | (.30) | . | (Ex. 11) |
| $C_8H_{17}$ | 1 | S | S | .64 | .92 | .121 | .158 | . | (Ex. 12) |
| $C_9H_{19}$ | 1 | S | S | .74 | — | .130 | .151 | — . | (Ex. 13) |
| $C_{10}H_{21}$ | 1 | S | S | .61 | — | .121 | .140 | . | (Ex. 14) |
| $C_{12}H_{25}$ | 1 | S | S | .69 | — | .127 | .137 | . | (Ex. 15) |

Phase & Phase Transition Temperature (°C.)

C represents solid, $S_B$ represents smetic B phase, $S_c*$ represents chiral smectic C phase, $S_A$ represents smectic A phase, I represents liquid, ( ) represents monotropic liquid crystal phase.

EXAMPLE 16

Preparation of a compound of formula (1a), wherein A=0, m, and n are 0,

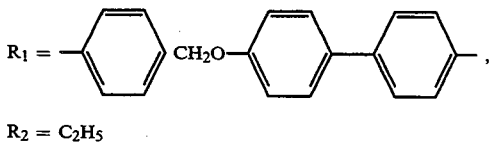

$R_2 = C_2H_5$

To a solution of 0.64 g (2.30 mmol) of 4,4'-biphenyl-monobenzyl ether and 0.2 g of KOH in 60 ml of ethanol was added dropwise 0.68 g (2.30 mmol) of the sulfonate prepared in Example 2. The mixture was refluxed for 24 hrs. After the mixture was cooled to room temperature, it was extracted with CH$_2$Cl$_2$ (3.50 ml). The organic phase was dried over Na$_2$SO$_4$ and concentrated. After flash chromatography (SiO$_2$, hexane/ethyl acetate=1:1), 0.65 g of the pure product was obtained as a colorless oil, 70% yield.

$[\alpha]_D^{23} = -16\epsilon$ (=1.0, CHCl$_3$)

EXAMPLE 17

Preparation of a compound of formula (Ia), wherein A=O, m and n are 0,

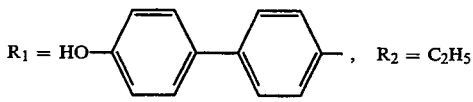

1.49 g of the product prepared in Example 16 was dissolved in ethyl alcohol. After hydrogenation of the solution and purification by column chromatography, 0.87 g (yield 75%) of the product was obtained.

$[\alpha]_D^{23} = -13.4°$ (C=1.19, CHCl$_3$)

EXAMPLE 18

Preparation of a compound of formula (Ib), wherein A=O, D=H, m=0, n=0, p=0, q=1, $R_2C_2H_5$, $R_3=C_{10}H_{21}$ A solution of 0.03 g (0.10 mmol) of 4-n-dodecanyloxybenzoic acid, 0.035 g (0.11 mmol) of the product prepared in Example 17, 0.04 g (0.20 mmol) of DCC and 0.01 g (0.01 mmol) of DMAP in 5.0 ml of CH$_2$Cl$_2$, was stirred at room temperature until the reaction was complete (monitored by TLC). Filteration and removal of the solvent of filtrate gave crude product which was then purified by flash column chromatography (SiO$_2$, CH$_2$Cl$_2$/hexane=1:1). The pure product was obtained as a colorless solid, 73% yield.

$[\alpha]_D^{23} = -12.6°$ (C=1.03, CHCl$_3$)

What we claim is:

1. An optically active organic compound has the following general formula:

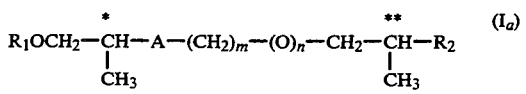

wherein A is O or S, R$_1$ is a hydrogen atom, an alkyl group having 1-22 carbon atoms, a hydroxy containing alkyl group, para-alkyl substituted phenyl, para-akyl substituted biphenyl, hydroxyphenyl, hydroxybiphenyl or tosyl; R$_2$ is an alkyl group having 2-8 carbon atoms; m is an integer of 0-5; n is 0 or 1, where when m=0, n is not 1, and * and ** are asymmetric centers.

2. An optically active organic compound as claimed in claim 1, wherein R$_1$ is a hydrogen atom, 4-hydroxyphenyl, or 4,4'-hydroxybiphenyl, 3. An optically active organic compound having the formula:

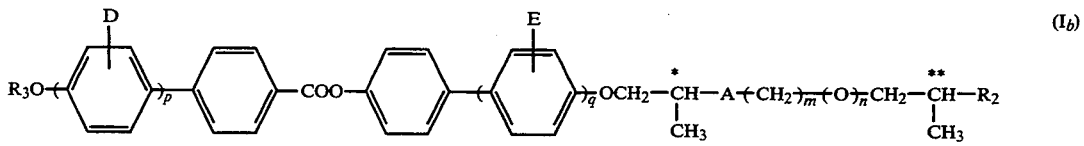

wherein A is O or S; R$_2$ is an alkyl group having 2-8 carbon atoms; m is an integer of 0-5; n is 0 or 1, where when m=0, n is not 1; p is 0 or 1; q is 0 or 1; D and E are independently H or a halogen atom; R$_3$ is a linear alkyl group having 1 to 22 carbon atoms; and * and ** are asymmetric centers.

4. An optically active organic compound as claimed in claim 3, wherein R$_3$ is a linear alkyl having 3-12 carbon atoms.

5. An optically active organic compound as claimed in claim 1, wherein A is O.

6. An optically active organic compound as claimed in claim 2, wherein A is O.

7. An optically active organic compound as claimed in claim 3, wherein A is O.

8. An optically active organic compound as claimed in claim 4, wherein A is O.

9. An optically active organic compound as claimed in claim 1, wherein m and n are O.

10. An optically active organic compound as claimed in claim 2, wherein m and n are O.

11. An optically active organic compound as claimed in claim 3, wherein m and n are O.

12. An optically active organic compound as claimed in claim 4, wherein m and n are O.

13. An optically active organic compound as claimed in claim 3, wherein D and E are H and F respectively.

14. An optically active organic compound as claimed in claim 4, wherein D and E are H and F respectively.

15. An optically active organic compound as claimed in claim 1, wherein $R_2$ is ethyl.

16. An optically active organic compound as claimed in claim 2, wherein $R_2$ is ethyl.

17. An optically active organic compound as claimed in claim 3, wherein $R_2$ is ethyl.

18. An optically active organic compound as claimed in claim 4, wherein $R_2$ is ethyl.

19. An optically active organic compound as claimed in claim 1, which has the following formula:

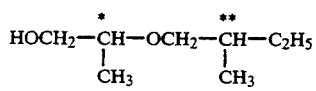

20. An optically active organic compound as claimed in claim 1, which has the following formula:

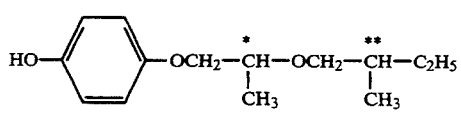

21. An optically active organic compound as claimed in claim 1, which has the following formula:

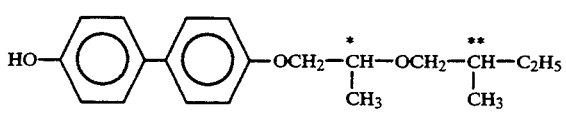

22. An optically active organic compound as claimed in claim 3, which has the following formula:

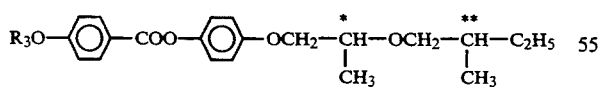

23. An optically active organic compound as claimed in claim 3, which has the following formula:

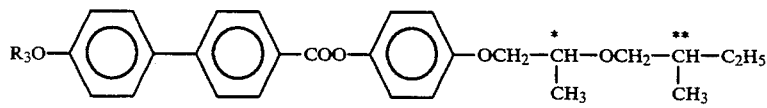

24. An optically active organic compound as claimed in claim 3, which has the following formula:

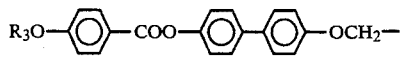
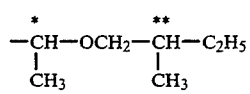

25. A liquid crystal composition comprising an optically active organic compound having the following general formula:

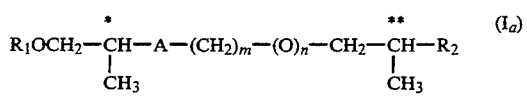
(I$_a$)

wherein A is O or S, $R_1$ is a hydrogen atom, an alkyl group having 1–22 carbon atoms, a hydroxy containing alkyl group, para-alkyl substituted phenyl, para-alkyl substituted biphenyl, hydroxyphenyl, hydroxybiphenyl or tosyl; $R_2$ is an alkyl group having 2–8 carbon atoms; m is an integer of 0–5; n is 0 or 1, where when m=0, n is not 1, and * and ** are asymmetric centers.

26. A liquid crystal composition comprising an optically active organic compound having the following general formula:

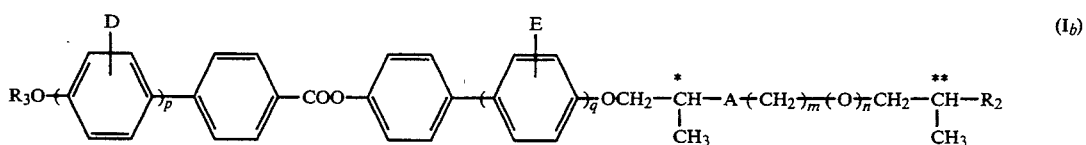
(I$_b$)

wherein A is O or S; $R_2$ is an alkyl group having 2–8 carbon atoms; m is an integer of 0–5; n is 0 or 1, where when m=0, n is not 1; p is 0 or 1; q is 0 or 1; D and E are independently H or a halogen atom; $R_3$ is a linear alkyl group having 1 to 22 carbon atoms; and * and ** are asymmetric centers.

27. A liquid crystal composition as claimed in claim 26, further comprising a liquid crystal mixture selected from the group consisting of smectic C phase liquid crystal or chiral smectic c phase liquid crystals.

28. A liquid crystal device comprising a pair of substrate plates and a liquid crystal composition provided between said substrate plates, said liquid crystal composition consisting of an optically active organic compound having the following formula:

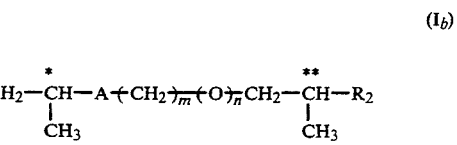
(I$_a$)

wherein A is O or S, $R_1$ is a hydrogen atom, an alkyl group having 1–22 carbon atoms, a hydroxy containing alkyl group, para-alkyl substituted phenyl, para-alkyl substituted biphenyl, hydroxyphenyl, hydroxybiphenyl

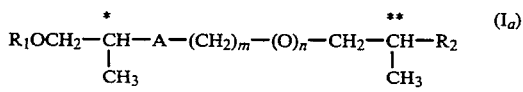

or tosyl; $R_2$ is an alkyl group having 2–8 carbon atoms; m is an integer of 0–5; n is 0 or 1, where when m=0, n is not 1, and * and ** are asymmetric centers.

* * * * *

UNITED STATES PATENT AND TRADEMARK OFFICE
CERTIFICATE OF CORRECTION

PATENT NO. : 5,366,656
DATED : November 22, 1994
INVENTOR(S) : Wen-Liang Tsai, et al.

It is certified that error appears in the above-indentified patent and that said Letters Patent is hereby corrected as shown below:

On Title Page, left column, item "73", "Prov." should be -- Republic--.

Signed and Sealed this

Twenty-first Day of March, 1995

Attest:

BRUCE LEHMAN

*Attesting Officer*      *Commissioner of Patents and Trademarks*